United States Patent [19]
Janzen et al.

[11] Patent Number: 5,830,130
[45] Date of Patent: *Nov. 3, 1998

[54] DEVICE AND METHOD FOR SEALING PUNCTURE WOUNDS

[75] Inventors: Ernst Janzen, Laren, Netherlands; Gunther Ruttgers, Stolberg, Germany; Lawrence Saper, New York; Sid Wolvek, Brooklyn, both of N.Y.

[73] Assignee: Datascope Investment Corp., Montvale, N.J.

[*] Notice: The term of this patent shall not extend beyond the expiration date of Pat. No. 5,391,183.

[21] Appl. No.: 318,380

[22] Filed: Oct. 5, 1994

Related U.S. Application Data

[60] Division of Ser. No. 746,339, Aug. 16, 1991, Pat. No. 5,391,183, which is a continuation-in-part of Ser. No. 634,478, Dec. 27, 1990, abandoned.

[30] Foreign Application Priority Data

Sep. 21, 1990 [EP] European Pat. Off. ............ 90 118 186

[51] Int. Cl.$^6$ .............................. A61B 17/08; A61D 1/00
[52] U.S. Cl. .............................. 606/213; 604/15; 604/60; 604/187; 604/218
[58] Field of Search ..................... 606/213, 215, 606/191; 604/11, 14–17, 46, 47, 52, 53, 57, 59, 60, 93, 158, 164, 171, 173, 310, 311, 285–288, 367, 368, 68, 181, 187, 183, 218; 602/43–53

[56] References Cited

U.S. PATENT DOCUMENTS

| | | |
|---|---|---|
| Re. 34,866 | 2/1995 | Kensey et al. . |
| 3,016,895 | 1/1962 | Sein . |
| 3,490,448 | 1/1970 | Grubb ........................ 602/53 |
| 3,572,335 | 3/1971 | Robinson . |
| 3,703,897 | 11/1972 | Mack et al. ................. 602/43 |
| 4,005,709 | 2/1977 | Laerdal ....................... 602/53 |
| 4,377,159 | 3/1983 | Hansen ....................... 602/53 |
| 4,578,061 | 3/1986 | Lemelson . |
| 4,588,395 | 5/1986 | Lemelson . |
| 4,619,261 | 10/1986 | Guerriero . |
| 4,638,803 | 1/1987 | Rand . |
| 4,744,364 | 5/1988 | Kensey . |
| 4,749,689 | 6/1988 | Miyata et al. .............. 604/368 |
| 4,790,819 | 12/1988 | Li et al. ...................... 604/59 |
| 4,838,280 | 6/1989 | Haaga . |
| 4,852,568 | 8/1989 | Kensey . |
| 4,878,906 | 11/1989 | Lindemann et al. . |
| 4,890,612 | 1/1990 | Kensey ....................... 606/213 |
| 4,895,564 | 1/1990 | Farrell . |
| 4,900,303 | 2/1990 | Lemelson . |
| 4,929,246 | 5/1990 | Sinofsky . |
| 4,941,874 | 7/1990 | Sandow et al. . |
| 4,950,234 | 8/1990 | Fujioka et al. . |
| 4,994,028 | 2/1991 | Leonard et al. . |
| 5,021,059 | 6/1991 | Kesey et al. . |
| 5,053,046 | 10/1991 | Janese . |
| 5,061,274 | 10/1991 | Kensey ....................... 606/213 |
| 5,108,421 | 4/1992 | Fowler . |
| 5,129,882 | 7/1992 | Weldon et al. . |
| 5,275,616 | 1/1994 | Fowler . |
| 5,292,332 | 3/1994 | Lee . |
| 5,391,183 | 2/1995 | Janzen et al. .............. 606/191 |
| 5,478,352 | 12/1995 | Fowler . |
| 5,591,204 | 1/1997 | Janzen et al. .............. 606/215 |
| B1 5,275,616 | 1/1996 | Fowler . |

FOREIGN PATENT DOCUMENTS

| | | |
|---|---|---|
| 2641692 | 7/1990 | France . |
| 8907370.3 | 9/1989 | Germany . |
| 1509023 | 4/1978 | United Kingdom . |
| 8911301 | 11/1989 | WIPO . |

*Primary Examiner*—Ronald Stright, Jr.
*Attorney, Agent, or Firm*—Lerner, David, Littenberg, Krumholz & Mentlik

[57] ABSTRACT

A device is proposed for inserting hemostatic material through a tissue channel and against the outside wall of a blood vessel of a patient, wherein the blood vessel wall has a puncture therein adjacent the tissue channel. The device includes a charge of hemostatic material and a hollow sheath adapted to pass through the tissue channel, the sheath having a cross sectional profile larger than the puncture. The device places the hemostatic material in the hollow sheath and advances the hemostatic material through the sheath to the outside of the vessel wall around the puncture.

16 Claims, 14 Drawing Sheets

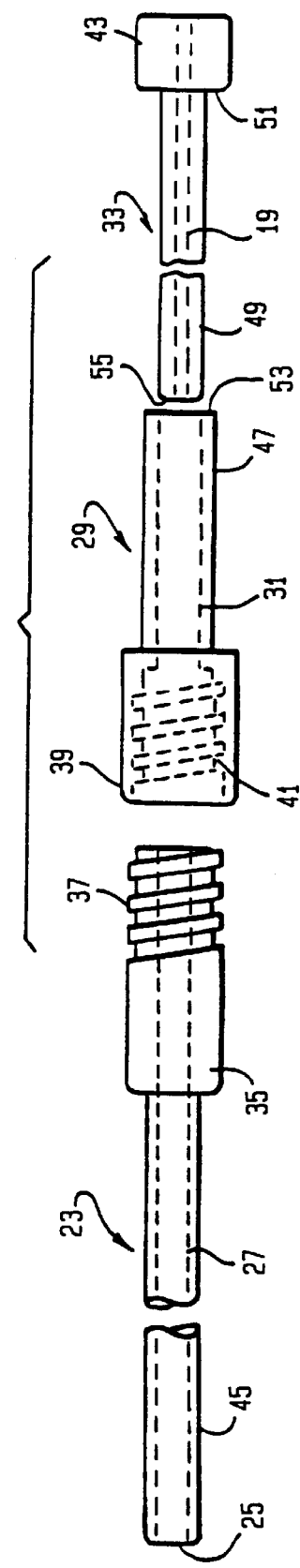
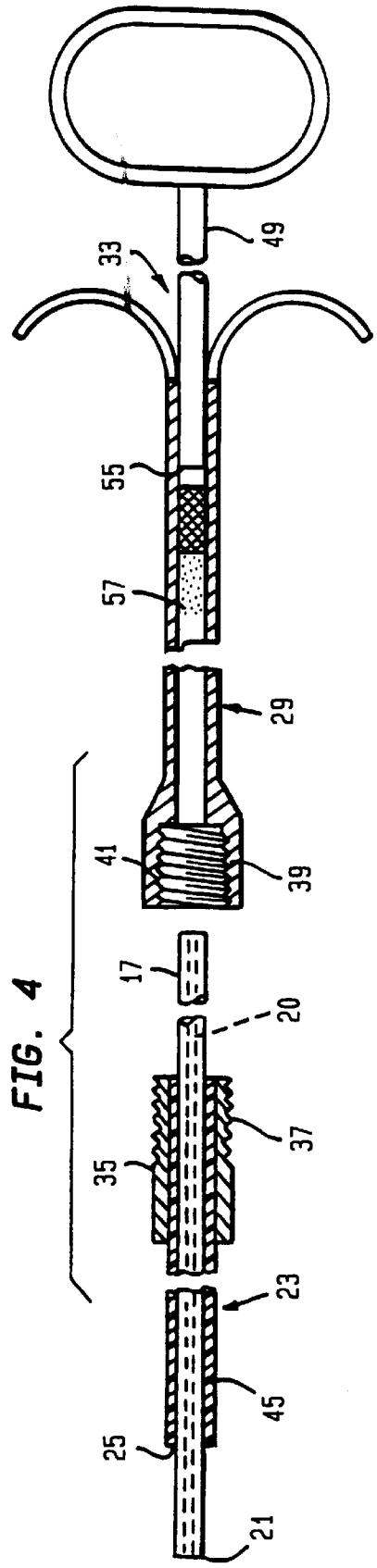

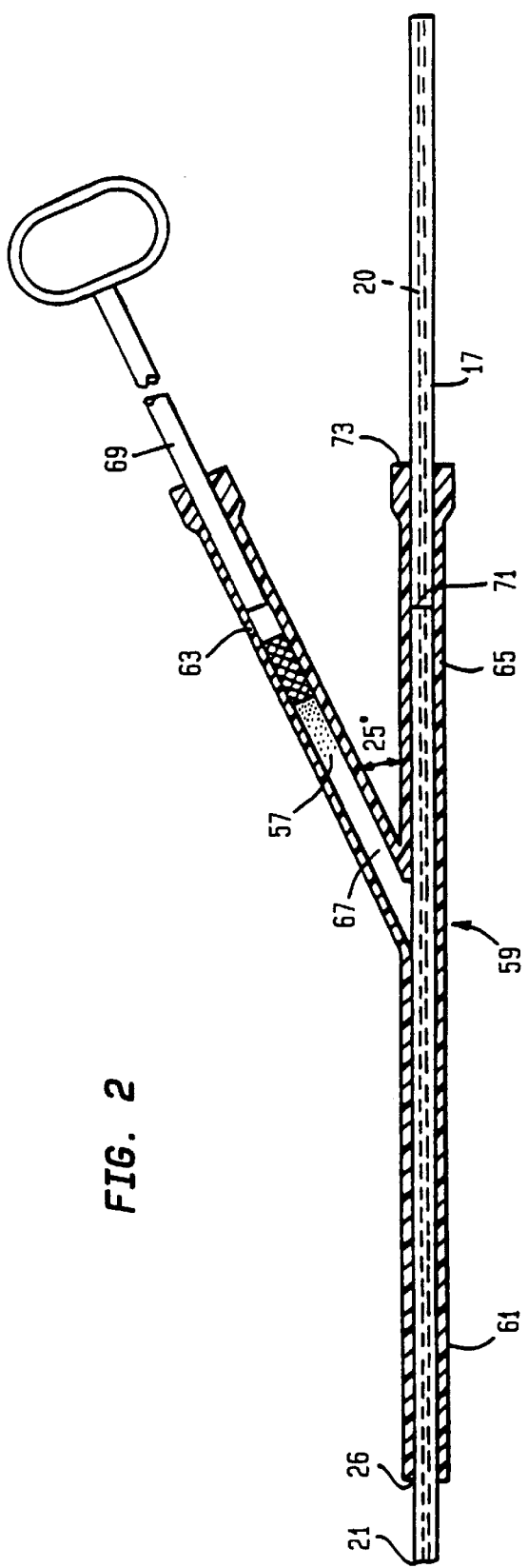

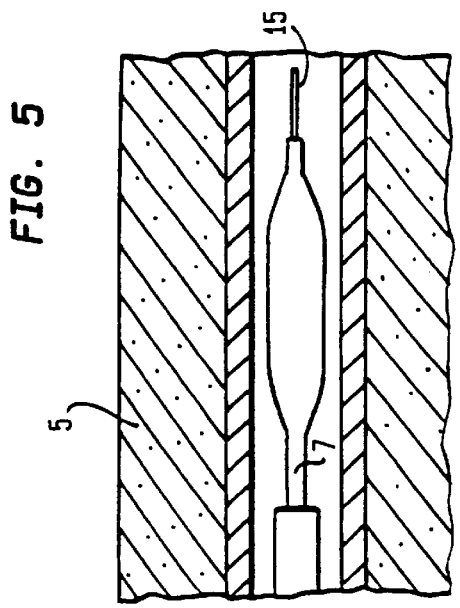
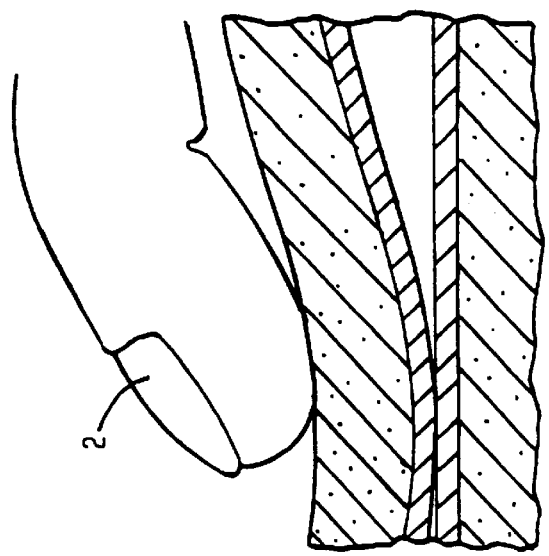
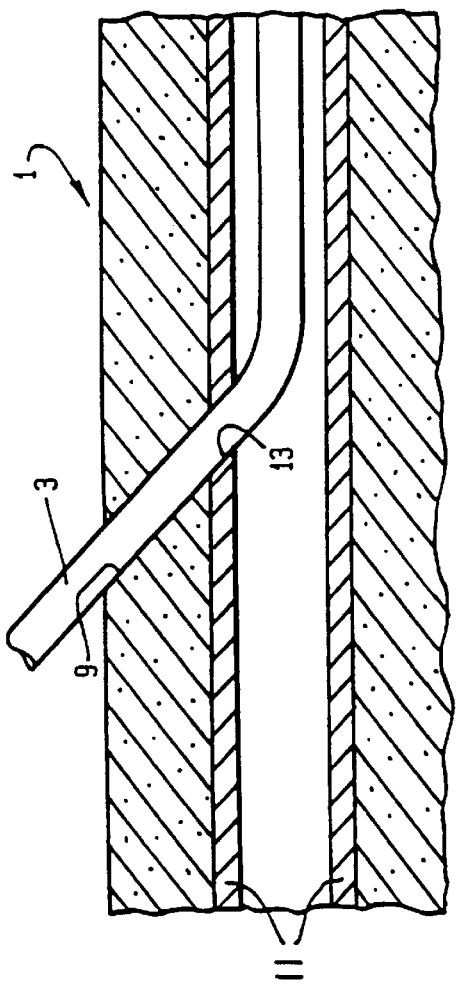
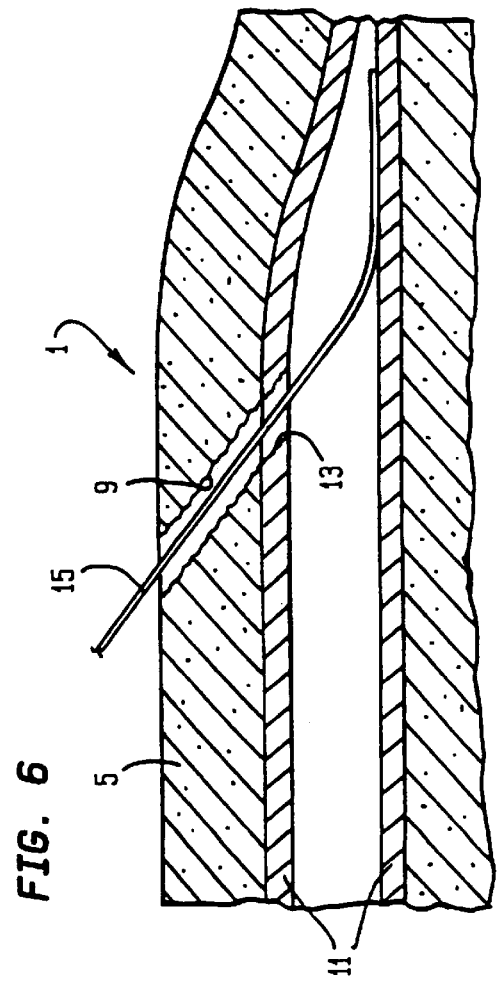
FIG. 5
FIG. 6

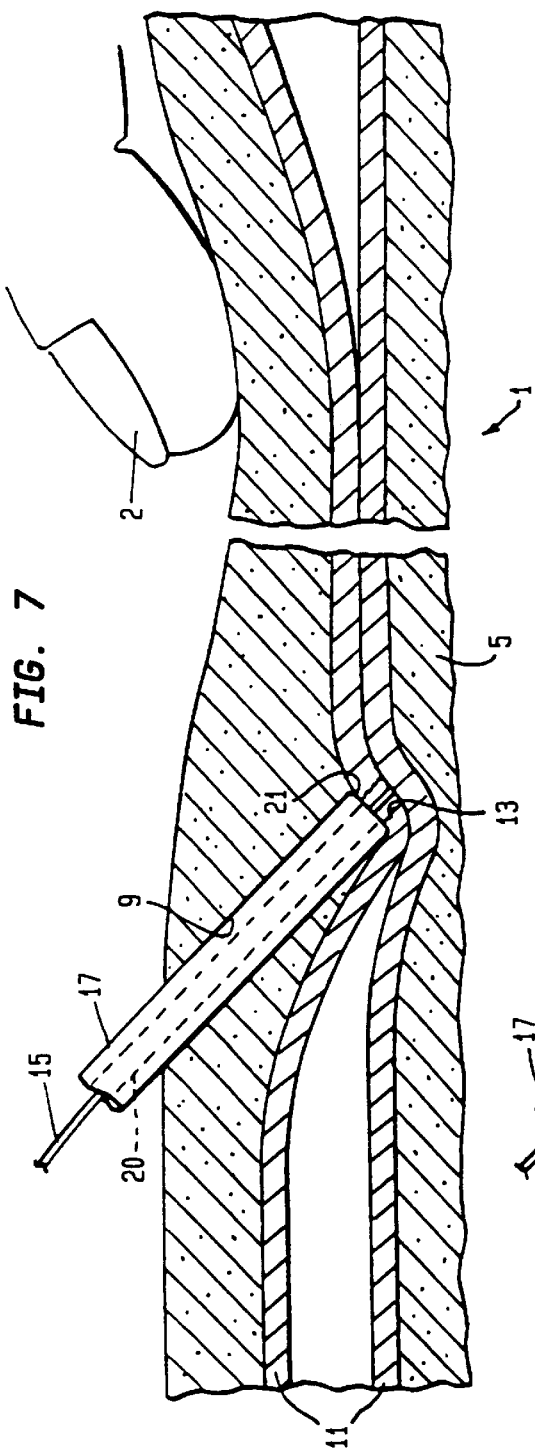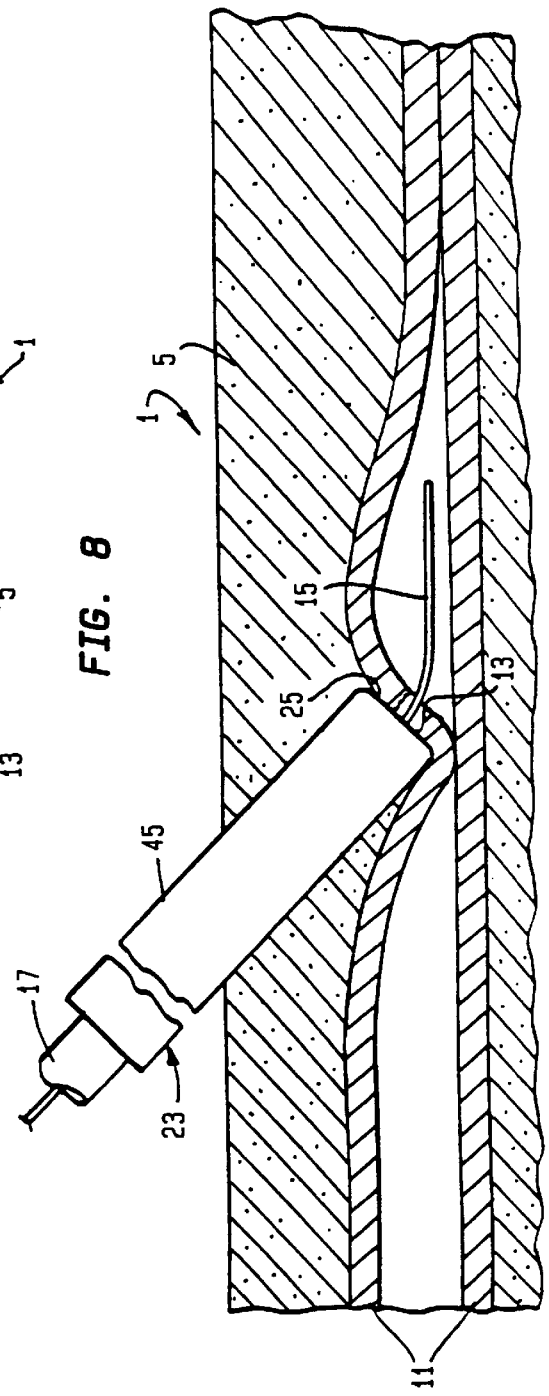

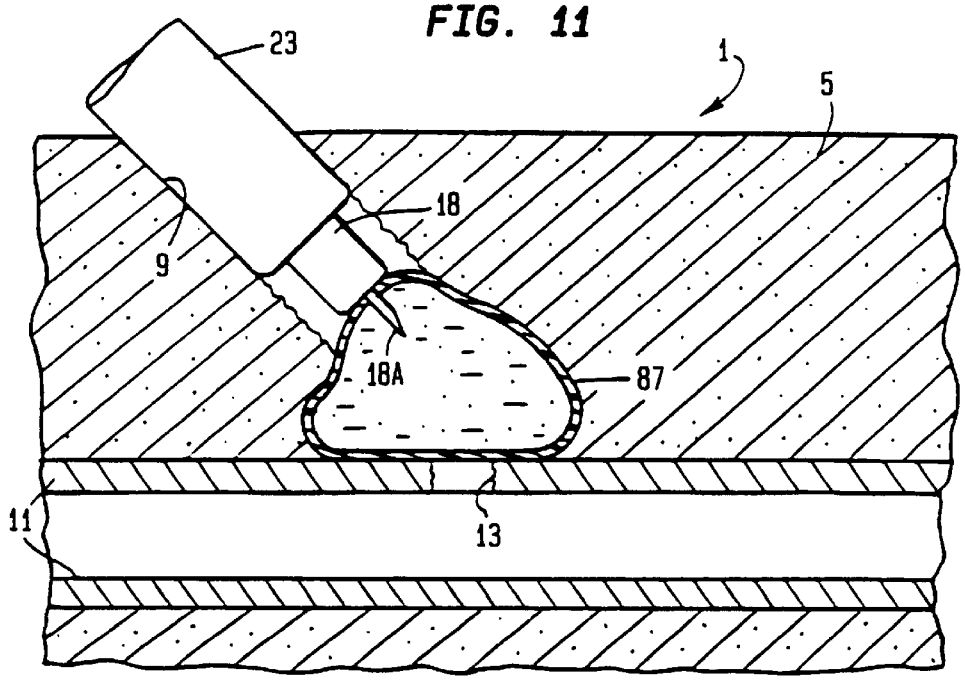
FIG. 11
FIG. 12A
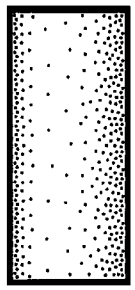
FIG. 12B
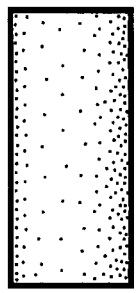
FIG. 12C
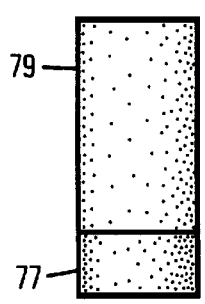
FIG. 12D
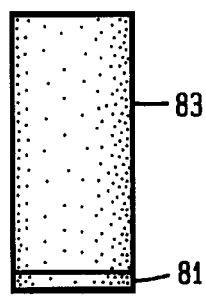
FIG. 12E
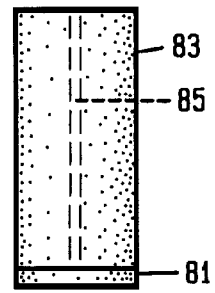

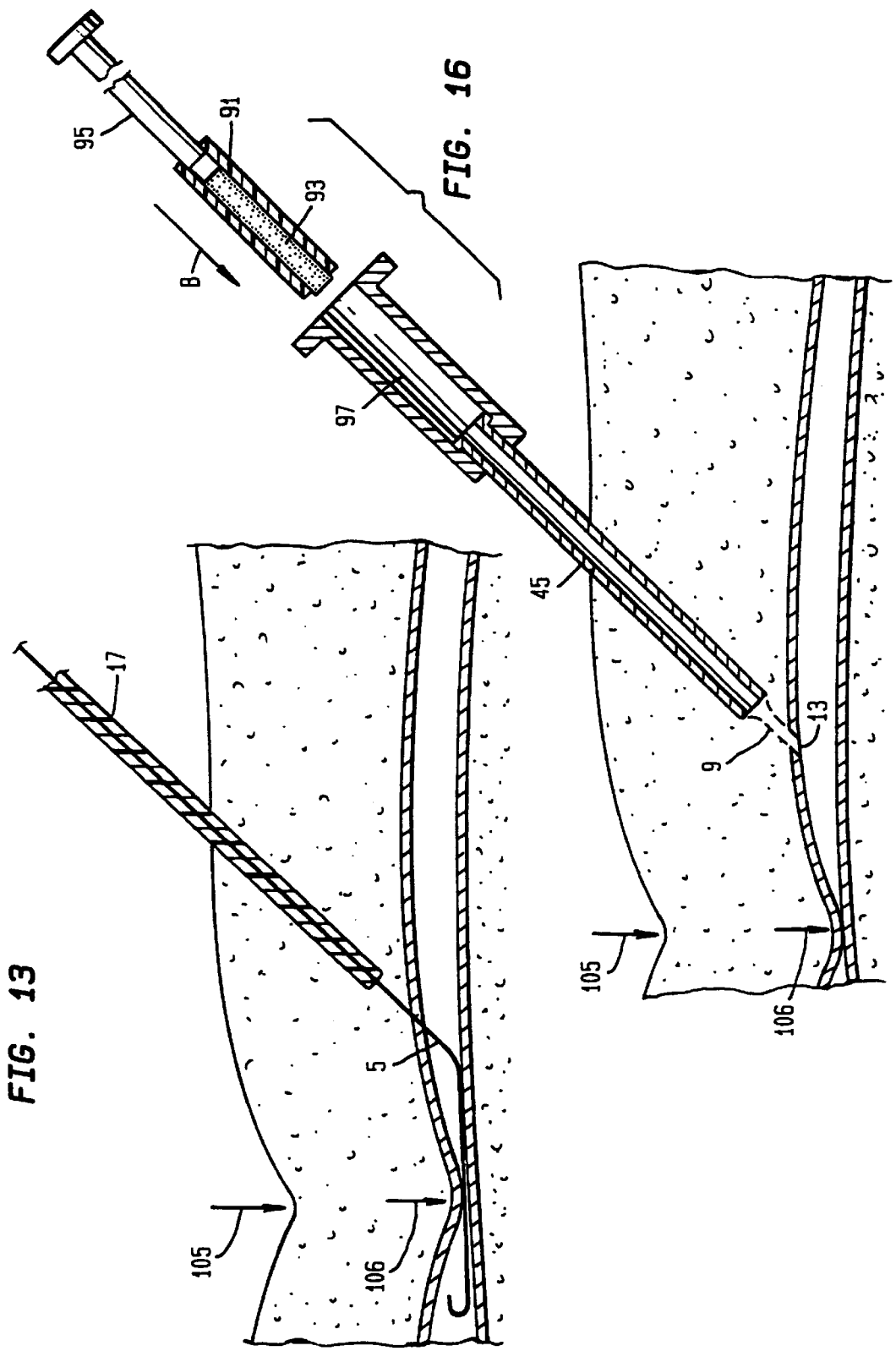

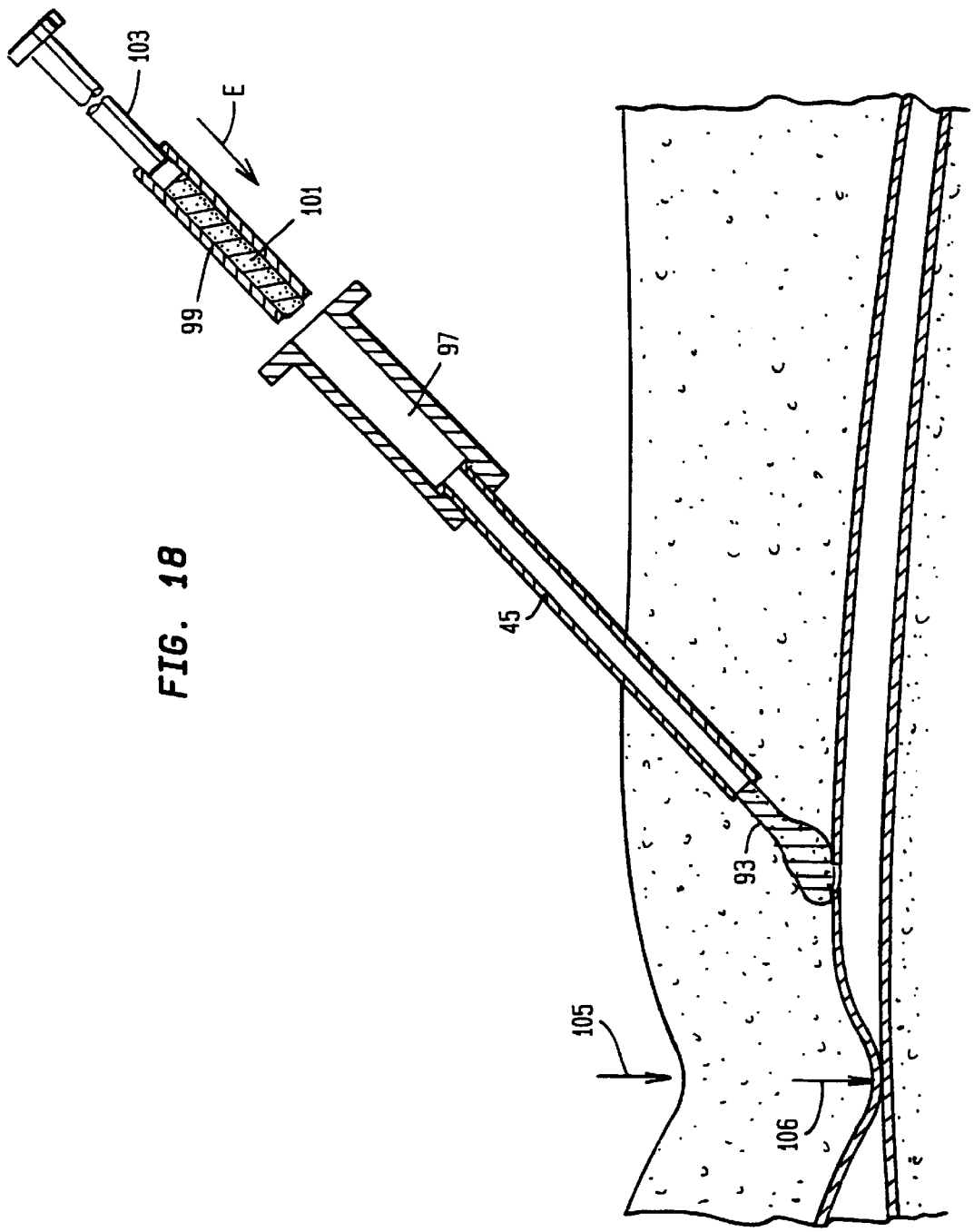

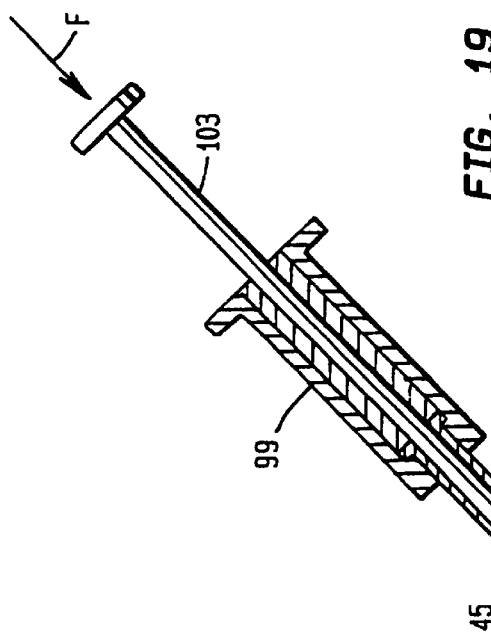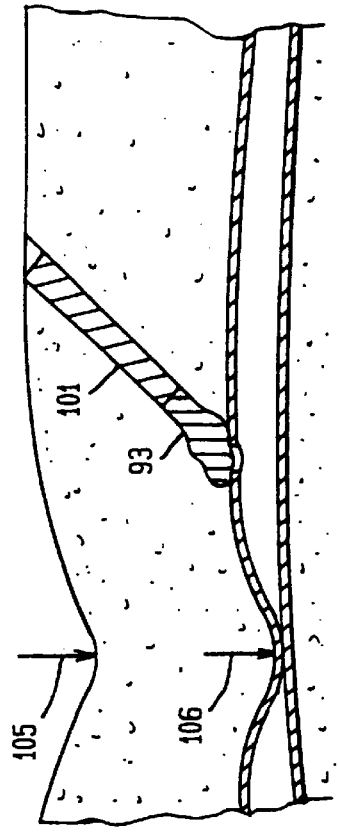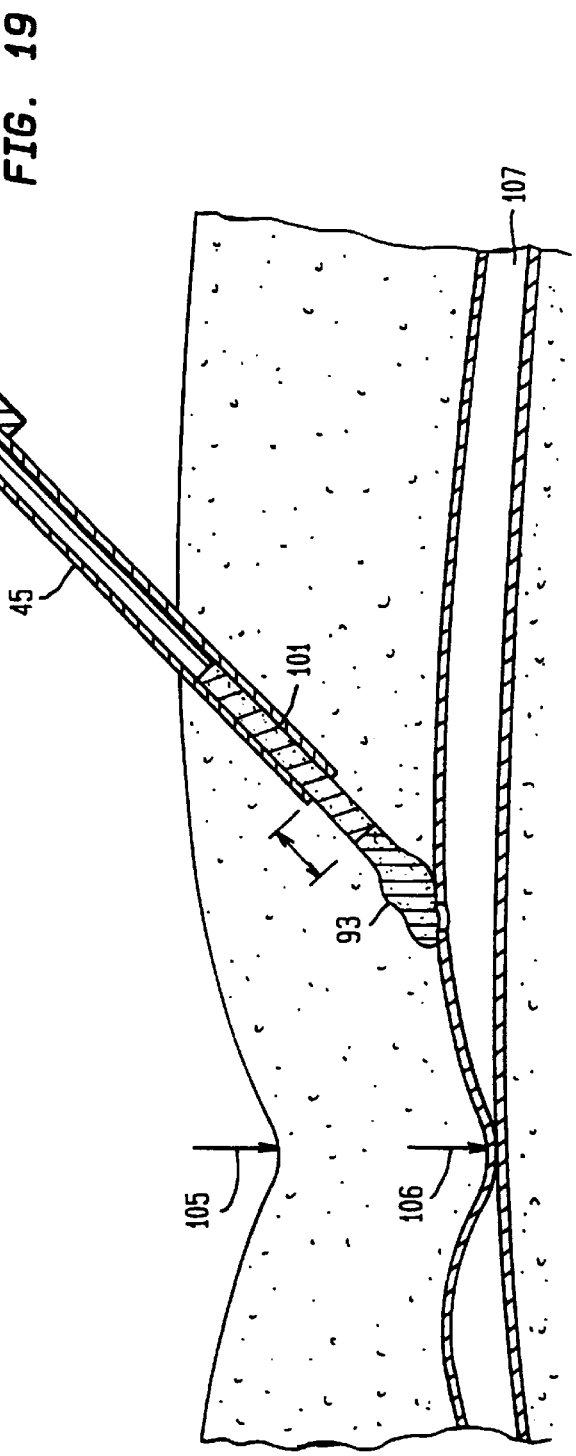
FIG. 19
FIG. 21

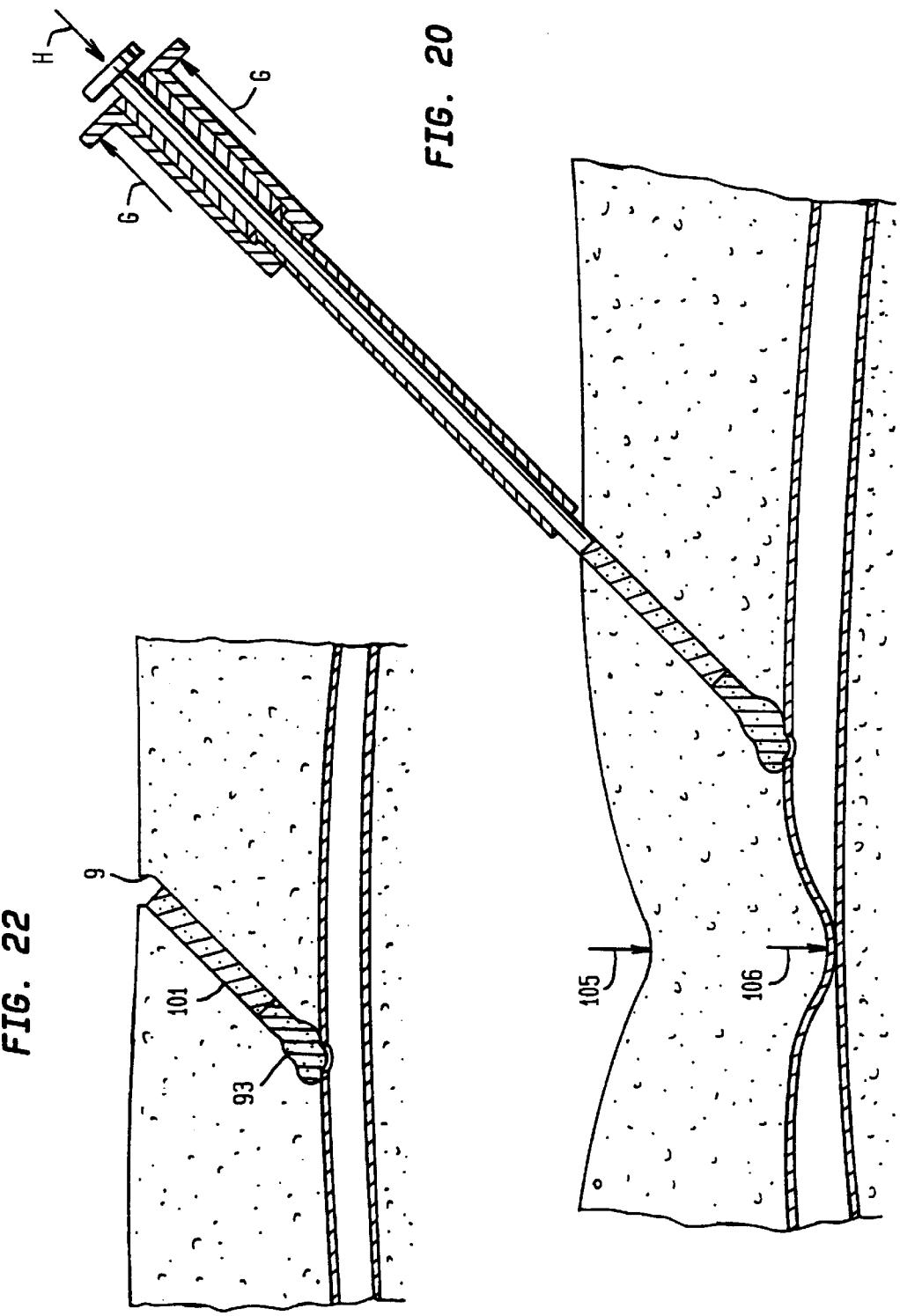

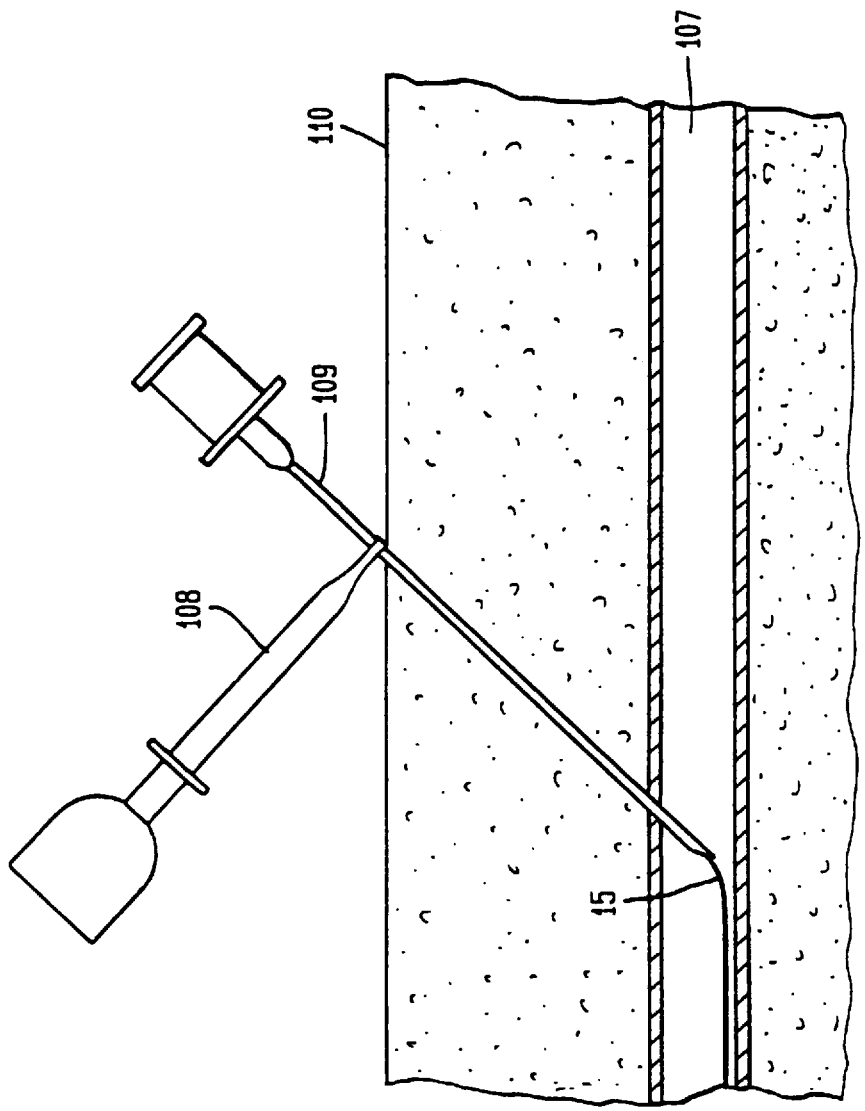

DEVICE AND METHOD FOR SEALING PUNCTURE WOUNDS

This application is a division of application Ser. No. 07/746,339 filed Aug. 16, 1991, now U.S. Pat. No. 5,391,198 which is a continuation-in-part of application Ser. No. 07/634,478 filed Dec. 27, 1990 and now abandoned.

BACKGROUND OF THE INVENTION

1. Field of the Invention

The present invention relates to a method for sealing a puncture wound in a blood vessel and a device for practicing said method.

2 Related Background

In certain medical procedures, such as cardiac catheterization, dilatation and counterpulsation, a catheter or other device is inserted into an artery, most commonly by percutaneous methods, and then fed through the arterial tree to the site where needed, frequently, the region of the heart. The site usually selected for insertion is the groin, because the femoral artery in that region is relatively easy to locate.

These procedures are normally initiated by insertion of an angiographic needle, followed by passing a guide wire through that needle into the artery. The needle is then removed leaving the guide wire in place. Next, a sheath-dilator set is passed over the guide wire into the artery in order to enlarge the opening sufficiently to permit entry of the catheter or other device. The dilator is then removed, leaving the sheath or guide cannula in place. The catheter or other device can then be inserted through the cannula with full confidence that when it emerges from the distal end it will be within the lumen of the artery.

It should be understood that the subject invention is independent of the nature of the medical device being used to treat the patient. Accordingly, the term "catheter" will be used here in a very generic and broad way to include not only "catheters" in the strict sense, but any device that is inserted into a blood vessel of the body.

Similarly, the subject invention is independent of the blood vessel involved. While it is anticipated that the femoral artery will be the most commonly used blood vessel, other arteries as well as veins might just as easily be involved.

After a procedure, for example, counterpulsation, has been completed, the sheath must be removed and the wound closed. Often, this can be accomplished simply by the application of digital pressure, generally augmented by the use of a pressure dressing. Customarily, pressure must be applied for at least ½ hour, and frequently for much longer than that. While pressure dressings often suffice, it is not uncommon for additional devices, such as sandbags, to be needed. In addition, during this period the patient must be immobilized, lest movement interfere with the closing process. Because of the pressure required, the time during which it must be applied and the need for immobilization, the procedure is painful and uncomfortable. It also requires prolonged personal attention of a health care professional. Finally, wound closures accomplished in this manner are prone to reopen unexpectedly long after closure appears to have been completed. Patients are therefore often required to remain in the hospital for 24 hours or longer.

Because sealing can be such a problem, cardiologists tend to use the smallest calibre catheters when performing catheterization procedures. Larger calibre catheters, however, are far preferable. An improved sealing procedure whereby larger catheters can be used without increasing the sealing difficulties would greatly facilitate cardiac catheterization.

A series of related devices which were designed to address some of these problems is described in U.S. Pat. Nos. 4,744,364, 4,852,568 and 4,890,612. These three patents describe a mushroom or umbrella shaped device which is used to seal the artery from the inside. The head of the device is placed within the arterial lumen and means are provided to pull and hold the underside of the head against the inside wall of the lumen. It is believed, however, that sealing from the inside can be the source of its own problems, including the promotion of clot formation inside the vessel.

Another method for sealing a puncture wound is described in U.S. Pat. No. 4,929,246. The approach taken there is to insert a balloon-tipped catheter into the tissue wound, inflate the balloon against the hole in the artery and then use a laser to thermally weld the wound closed.

The present invention is believed to overcome most of the drawbacks of the traditional method, without creating any new difficulties. This is accomplished by using a plug, preferably a collagen plug or plug of some other resorbable material, to seal the artery along its outside wall.

SUMMARY OF THE INVENTION

In its most simplified form, the instant invention involves the placing of hemostatic material against the outside wall of a punctured artery. The hemostatic material covers the entire puncture site and a hemostatic seal is formed so as to stop bleeding from the puncture wound.

In one embodiment, the subject invention teaches the use of a plug, preferably of fibrous collagen material. The plug is inserted into the tissue wound and is held against the outside of the artery wall so as to overlap the puncture wound. Before plug insertion, the artery is preferably clamped by the use of external digital pressure, at a point slightly upstream of the wound site. After the plug has been inserted, the upstream clamping pressure is maintained for a very short period of time, and then gently removed. Slight pressure may be maintained on the plug to hold it against the artery wall until a good seal has been established.

In order to insert the plug in accordance with the procedure outlined above, a special device has been designed. It is comprised of two basic components, a sheath and a plug pusher or piston. The sheath is inserted through the tissue until its leading end is near to or abuts the outer wall of the artery. Thereafter, the plug is advanced through the sheath by use of the plug pusher until the plug abuts the artery wall and overlaps the arterial puncture on all sides. Finally, after a good seal has been established, the sheath and pusher are removed.

BRIEF DESCRIPTION OF THE DRAWING

FIG. 1 is an exploded view of one embodiment of an insertion apparatus in accordance with the instant invention.

FIG. 2 depicts, in cross section, one embodiment of an insertion apparatus in accordance with the instant invention.

FIG. 3 depicts, in cross section, a second embodiment of an insertion device in accordance with the instant invention.

FIG. 4 depicts, in cross section, an exploded view of a third embodiment of an insertion apparatus in accordance with the instant invention.

FIG. 5 is an enlarged, schematic drawing, in cross section, of an insertion site, showing a balloon catheter, having passed over a guide wire through a guide cannula into the femoral artery of a patient.

FIG. 6 shows the insertion site of FIG. 5 after the catheter and cannula have been removed.

FIG. 7 shows the insertion site of FIG. 6 after insertion of a tissue dilator in accordance with the instant invention.

FIG. 8 shows the insertion site of FIG. 7 after insertion of a sheath over the tissue dilator in accordance with the instant invention.

FIG. 11 shows an alternative embodiment of the instant invention wherein a collagen balloon is used to seal an arterial puncture.

FIGS. 12a, b, c, d and e show alternative forms of plug which are useful in practicing the instant invention.

FIGS. 13 through 23 show the steps of an alternate procedure for practicing the instant invention.

DETAILED DESCRIPTION

Figure 9:
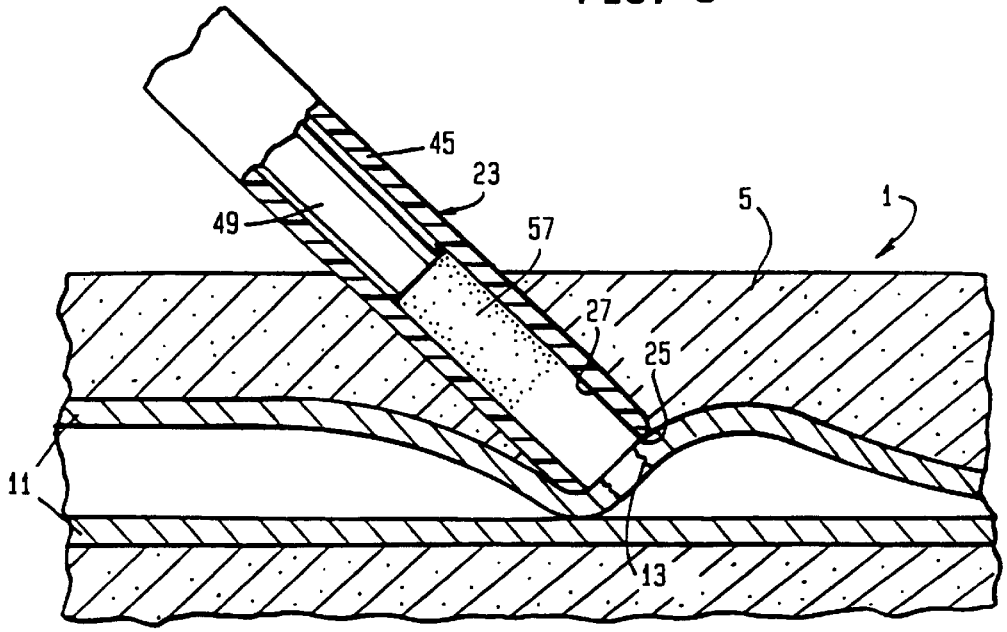
FIG. 9 shows the insertion site of FIG. 8 after removal of the tissue dilator and guide wire and after partial insertion of a hemostatic plug and plug pusher.

In certain procedures, for example, intra-aortic balloon pumping ("IABP"), percutaneous transluminal coronary angioplasty ("PTCA") and angiography, as best seen in FIG. 5, a catheter or other device 7 is inserted, often over a guide wire 15, through a guide cannula 3 into an artery 11, most frequently, the common femoral artery in the groin area of the patient's leg 1. When the procedure (e.g., counterpulsation) has been completed, the device (e.g., the catheter), the guide wire and the guide cannula must be removed and the wound closed.

In accordance with one embodiment of the instant invention, wounds of this type are closed by inserting a plug into tissue wound or channel 9, and holding it against the outside of the artery wall over arterial puncture 13 for a short period of time until a good self-sustaining hemostatic seal is established. Although punctures of the sort made by percutaneous procedures will generally, after removal of all cannulas and catheters, be in the nature of slits, for ease of understanding, they are depicted in the drawings herein more as holes. The shape of the puncture, however, is not critical.

In order to insert the plug to assure that it is properly located and to be able to hold it in place until a good seal is established, a special insertion apparatus has been designed. One embodiment (FIG. 1) of an insertion apparatus according to the instant invention is comprised of a sheath assembly 23, a plug holder 29 and a plug pusher 33. Sheath assembly 23, in turn, is comprised of an elongated tubular sheath 45 and a collar 35. At its rear end, collar 35 is provided with an external thread 37. In addition, sheath assembly 23 is provided with a sheath channel 27, which runs through the entire assembly, from front end 25, through sheath 45 and through collar 35.

Plug holder 29 is comprised of an elongated rear tubular portion 47 and a coupling 39 which has an internal thread 41. Plug holder 29 also has a channel 31 running throughout its entire length. Coupling thread 41 is designed to mate with collar thread 37 so that when collar 35 is screwed into coupling 39, channels 31 and 27, which preferably are of the same cross sectional size and configuration, are aligned.

Like the other two components, the plug pusher 33 is also comprised of two parts, an elongated piston 49, and a stop knob 43. Piston 49 has a cross sectional size and configuration so as to permit sliding passage into channels 31 and 27 with only minimal clearance. The length of piston 49 is such that when sheath assembly 23 and plug holder 29 are screwed tightly together, shoulder 51 of knob 43 will abut rear end 53 of plug holder 29 as front end 55 of piston 49 is aligned with front end 25 of sheath 45.

It should be noted that pusher 33 is provided with its own channel 19. This is to permit passage therethrough of a guide wire and hence to enable pusher 33 to serve dual functions, as a tissue dilator and as a plug pusher.

In accordance with the method of the instant invention, first the device 7 (e.g., the IAB) and the guide cannula 3 are removed, leaving the guide wire 15 in place (as seen in FIG. 6). If no guide wire has been employed, prior to removal of the catheter and cannula, a guide wire may be inserted. As the cannula is withdrawn, in order to prevent bleeding, the artery is clamped, usually by pressing a finger 2 over the femoral artery upstream of the wound site. Because of this clamping, there is no significant blood pressure inside the artery at the site of the puncture (other than some small retrograde pressure) and the artery tends to collapse.

Although it is believed preferable to employ a guide wire, it is possible to practice the invention without one. It is also possible to practice the instant invention by eliminating the dilator, but this too is not the preferred approach.

The artery is clamped at least in part to prevent tissue channel 9 from filling with a pool of blood. When loose fibrous collagen encounters a pool of blood it tends to disintegrate almost immediately. Obviously, once disintegrated it cannot function properly to seal the arterial puncture. Hence, when collagen in loose fibrous form is employed, clamping of the artery is important. It is less important, but still generally advantageous, if the loose fibrous material has been tamped down or otherwise compressed. As used herein, the term "loose" includes material which has been compressed or tamped down.

Collagen that is more densely packed does not disintegrate upon encountering blood nearly as quickly as loose fibrous collagen. Therefore, clamping of the artery is not nearly as important when the hemostatic material is in the form of a densely packed material, as it is when a loose fleece-type hemostatic material is employed. Thus, although clamping is believed to be desireable, it is not, in all cases essential.

While the artery remains clamped, the proximal end of guide wire 15 is fed through channel 20 of tissue dilator 17. The physician can then slide the dilator down along the guide wire into tissue channel 9 until it reaches the wall of artery 11 (as depicted in FIG. 7).

The size and shape of the tissue dilator are such as to ensure that the body thereof will not enter the artery. In terms of size, preferably a dilator is selected which is significantly larger than the original guide cannula 3. With respect to its shape, unlike more traditional dilators which often have long tapered forward ends, the tissue dilator 17 of the instant invention has a blunt forward end 21. Although end 21 may be slightly rounded or chamfered in order to facilitate smooth passage through tissue channel 9, it is preferable not to reduce it in size sufficiently to permit entry through the arterial puncture 13 into the lumen of the artery.

As noted above, during this phase of the procedure, there is no significant blood pressure in the region of artery 11 adjacent puncture 13. As a result, when end 21 of dilator 17 reaches artery 11, the wall of the artery tends to collapse further (as depicted in FIG. 7). The physician knows that the dilator has reached the artery because a noticeable increase in resistance is felt.

According to the procedure of the instant invention, once increased resistance is encountered, axial pressure is maintained so as to hold end 21 of dilator 17 against artery 11. Next, a sheath 45 is passed over dilator 17 and advanced along the dilator again until increased resistance is encountered. As with the dilator, increased resistance indicates that front end 25 is against artery 11 (as depicted in FIG. 8). In addition, a marker can be placed around the circumference of the dilator to signal when the distal end of the sheath is aligned with the distal end of the dilator.

Because end 25 of sheath 45 is larger than arterial puncture 9, the sheath cannot enter the arterial puncture. Although the precise dimensions of dilator 17 and sheath 45 are not critical, it is believed desirable that the sheath 45 be 30% to 50% or more larger than the previously removed guide cannula 3. In clinical trials done to date, when the guide cannula was 9 Fr., a 13 Fr. tissue dilator and a 14 Fr. sheath were used. It should be understood, however, that cannulae which are oversized by as little as 10% may also be suitable.

Once the guide or procedure cannula has been removed, tissue channel 9 tends to collapse. Also, once the procedure cannula and the procedure catheter have been removed, arterial puncture 13 has a tendency to close up. It may therefore be possible or even preferable to use a sheath that is the same size as or even smaller than the previously removed procedure cannula.

With the front end 25 of sheath 45 held snugly against the wall of artery 11, plug 57 is slid down through lumen 27 of sheath 45 (as shown in FIG. 9) until it reaches end 25 of sheath 45 where it encounters artery 11. If an insertion apparatus like that shown in FIG. 1 is used, plug 57 is initially housed in plug holder 29. When it is time for plug insertion, holder 29 is screwed onto sheath assembly 23 by means of threads 37 and 41, and piston 49 is inserted into channel 31. Advancement of the piston then forces plug 57 from holder 29 into sheath 45 and through lumen 27 to the artery wall.

Figure 10:
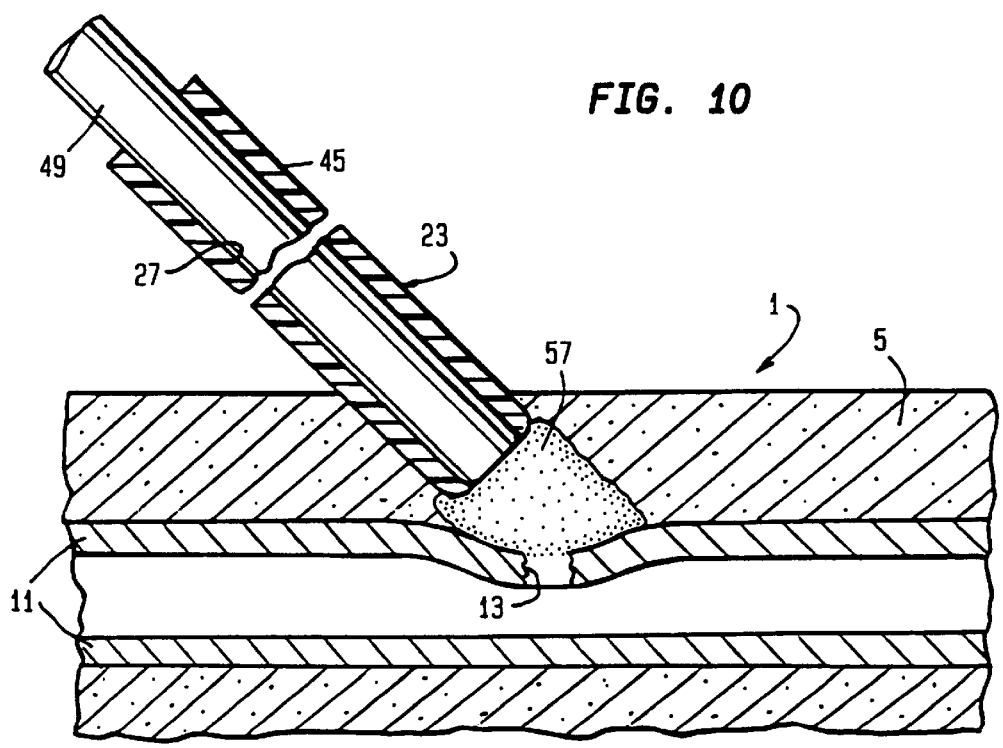
FIG. 10 shows the insertion site of FIG. 9 after the hemostatic plug has been pushed out of the sheath and while it is being held in intimate contact with the arterial puncture.

Once resistance is felt, the physician slowly withdraws the sheath while continuing to maintain pressure against the piston so that plug 57 remains pressed against artery 11. When shoulder 51 of knob 43 abuts rear end 53 of holder 29, the physician knows that plug 57 has been pushed entirely out of lumen 27 (as shown in FIG. 10). Axial pressure is maintained for a short period of time, perhaps as little as one minute or as long as five minutes, depending upon the circumstances, to allow plug 57 to seat in tissue channel 9 and against arterial puncture 13. Minimal axial pressure is thereafter continued while clamping pressure is slowly released until a good self-sustaining hemostatic seal has been confirmed. The sheath, holder, and pusher can all then be removed.

While it is believed that the preferable procedure is to permit both piston and sheath to remain in place until a self-sustaining hemostatic seal has been achieved, this is not absolutely necessary. Some physicians may prefer, once the pressure of the plug against the artery wall has produced hemostasis, to withdraw the sheath so that the tissue wound may begin to close down, while maintaining pressure on the plug by use of the piston alone. Alternatively, the piston might be withdrawn and reliance placed upon the outer rim of the sheath to hold the plug against the artery wall and assure hemostasis in that manner.

In addition, removal of the piston without removal of the sheath permits insertion of a second plug. This might be necessary where the first plug, perhaps of a loose fibrous material, disintegrates upon encountering a pool of blood. A second plug, this one of more densely packed material having greater physical integrity and less of a tendency toward immediate disintegration, is inserted in the sheath and the piston reinserted behind it.

An apparatus similar to that of FIG. 1 is depicted in FIG. 4. The primary difference between the two is that the plug pusher of the FIG. 4 embodiment does not serve a dual function. Instead, the embodiment of FIG. 4 has a separate tissue dilator 17 with channel 20 running throughout its length.

Another, somewhat different embodiment of an apparatus for inserting a plug in accordance with the instant invention is depicted in FIG. 2. The insertion apparatus 59 of that embodiment is made in the form of a Y, with a common or sheath leg 61, a plug leg 63 and a dilator leg 65.

In one method of using the apparatus of FIG. 2, tissue dilator 17 and insertion apparatus 59 are preassembled by passing the dilator through legs 65 and 61 until enough of dilator 17 extends beyond the forward end of leg 61 to assure that end 21 will abut artery 11 before front end 26 of leg 21 reaches the surface of the patient's leg. The proximal end of the guide wire is then fed through dilator channel 20 and the dilator is slid down the guide wire into tissue wound 9 until end 21 of dilator 17 reaches the wall of artery 11. While holding the dilator against the artery wall, the physician slides insertion apparatus 59 along dilator 17 until end 26 of leg 61 reaches artery 11.

With end 26 held snugly against artery 11, dilator 17 is withdrawn, but only far enough so as to uncover channel 67 of plug leg 63. Plug pusher 69 is then moved down through channel 67 until plug 57 has entered common leg 61 and pusher 69 is then withdrawn so that it will not interfere with dilator 17 as it passes from leg 65 into leg 61.

Once plug 57 has entered leg 61 and pusher 69 has been retracted, dilator 17 is again advanced into leg 61. When resistance is encountered, the physician knows that plug 57 has reached the artery. While maintaining axial pressure on dilator 17, apparatus 59 is slowly withdrawn until proximal end 73 of leg 65 reaches indicator mark 71. The distance between indicator 71 and dilator end 21 is the same as the distance between proximal end 73 and forward end 26. Therefore, the physician knows that when mark 71 reaches end 73, all of plug 26 has exited from end 26 of leg 61. As was described in connection with the embodiment of FIG. 1, pressure is then maintained until a good self-sustaining hemostatic seal has been established.

The embodiment of FIG. 3 is very similar to that of FIG. 1, except that the dilator and plug legs have been transposed. In the FIG. 3 embodiment, plug leg 74 is coaxial with common leg 61 and dilator leg 75 is at an angle, whereas in the FIG. 2 embodiment the reverse is true.

Although it is believed that the preferred method for using the embodiment of FIG. 2 is to preassemble dilator 17 in apparatus 59, that is by no means necessary. If the physician prefers, he can just as well insert dilator 17 into tissue channel 9 as was described above in connection with the embodiment of FIG. 1. He can then pass leg 61 over it. With the embodiment of FIGS. 4 and 1, while it is believed preferable to insert dilator 17 first, the physician, if he prefers, can preassemble the dilator in the sheath before passing the dilator over the guide wire.

While plug 57 may be made of any resorbable material, collagen is believed to be most suitable. The physical form of the plug may vary widely, with the one selected by the physician being dependent upon the circumstances of the case. For example, where the puncture wound is relatively small and the patient has not been on high doses of anticoagulant and heparin, a plug, like that depicted in FIG. 12a, of loose fibrous material, somewhat like fleece or absorbent cotton or oxygenated cellulose, would serve quite well. Alternatively, for larger wounds in patients who have been on anticoagulants and heparin, it may be necessary that the plug be able to maintain some structural integrity for a longer period of time. Under those circumstances, a plug of more densely packed material, as depicted in FIG. 12b, might be preferred.

A third embodiment of a suitable plug is depicted in FIG. 12c. In that embodiment, the front end 77 of the plug might be of loose fibrous material, like that depicted in FIG. 12a, whereas the remainder 79 could be made of a more densely packed material.

Yet another type of plug is shown in FIG. 12d. In this configuration, the front end 81 is a collagen membrane and the remainder 83 is an expandable collagen sponge.

It is believed that when a collagen sponge or a densely packed collagen material are employed, very little if any pressure need be applied after the initial seating of the plug. This is believed to be true because the physical characteristics of the sponge-like or densely packed plug and the expansion thereof, as well as its interaction with body fluids in the tissue channel will be adequate to hold the front end against the artery wall.

It is also believed that, initially, when the plug is pressed against the artery, hemostasis is achieved by mechanical means, i.e., by application of mechanical pressure all around the arterial puncture. Shortly thereafter, however, the hemostatic material begins to bind to the arterial tissue and biochemical hemostasis takes over. Once biochemical hemostasis becomes sufficiently strong to withstand the normal blood pressure within the artery, and therefore self-sustaining, external mechanical pressure can be removed.

FIG. 12e shows yet another form of plug, similar to the plug of FIG. 12d, but with a lumen 85. This form of plug is designed for use by physicians who prefer not to remove the guide wire immediately after a procedure. The proximal end of the guide wire 15 can be fed through lumen 85 and through the collagen membrane 81. The plug is slid down along the guide wire through tissue channel 9 until its front end reaches the wall of the femoral artery. Indeed, the plug of FIG. 12e could even be inserted without the use of a sheath. When the wire 15 is withdrawn, the collagen membrane automatically reseals itself.

As noted earlier, the sheath is substantially larger in cross section than is arterial puncture 13. Consequently, when plug 57, which fills the entire cross section of the sheath channel, reaches the artery, even in its compressed state it overlaps puncture 13 on all sides. Obviously, then, when it exits the sheath and is permitted to expand, a full bandage-like covering over puncture 13 is assured.

In practice it has been found that when using a collagen plug in accordance with the subject invention, a good hemostatic seal can be achieved in five minutes or less. With larger wounds, for example, ones left after removal of 14 Fr. or larger catheters, or after the use of anticoagulants and heparin, sealing may take somewhat longer.

FIG. 11 depicts another means for practicing the instant invention. In this embodiment a piston 18 pushes ahead of its front end a closed balloon 87 formed of a collagen membrane and only partially filled with a collagen substance and a saline solution. The piston 18 has an injection needle 18a on its front end which pierces the balloon during the pushing action.

After the balloon 87 exits from the sheath 23 and is pressed against the wall of the artery 11, an inflation fluid is injected via the needle 18a to fill and expand the balloon, as shown in FIG. 11, so that the balloon covers the arterial puncture 13 and fills the region of tissue channel 9 immediately adjacent the arterial puncture 13. The piston 18 is thereafter retracted to withdraw the injection needle 18a from the balloon 87. The membrane which forms the balloon 87 then automatically reseals itself to hold the balloon in the inflated condition shown in FIG. 11. The sheath 23 and piston 18 may then be withdrawn. When using this embodiment, the inflation fluid itself should be resorbable, preferably a saline solution or saline mixed with collagen in solution.

As noted above, when the procedure cannula is removed, both the arterial puncture 13 and the tissue channel 9 tend to close up somewhat. The method depicted in FIG. 13 through 22 is designed to take advantage of this tendency. In the FIGS. 13–22 method, neither the hemostasis sheath 45 nor the dilator 17 are pushed through channel 9 all the way to arterial puncture 13. Instead, as shown at 89 in FIGS. 14, 14A, 15 and 15A they are inserted no further than to within about ¾ cm. of the artery.

First, digital pressure (see arrows 105 in FIGS. 13–21) is applied upstream of the wound so as to close down the artery (see arrows 106). In this way the pressure in the artery at the puncture site 13 is no more than about atmospheric pressure. Although the method of this invention could be practiced without applying digital pressure, that would likely result in more profuse bleeding.

Then, as shown in FIG. 13, the dilator 17 is inserted over guide wire 15 to about ¾ cm from puncture 13. It will generally be inserted so that between about 3 and about 6 cm. of its length is beneath the surface of the skin.

One method for assuring that the sheath is inserted to the proper depth is as follows. Once the artery 107 has been punctured and the guide wire is in place, a needle clamp 108, as is depicted in FIG. 23, is placed on the needle 109 at the skin line 110. With the clamp in place, the needle is removed from the patient. The needle can then be placed along side the sheath and a mark made on the sheath to indicate the distance from needle tip to needle clamp. Alternatively, a mark can be made ½ or ¾ cm. closer to the distal end of the sheath. As yet another alternative, a kit can be provided of variable length sheaths, each having a hub at one end, and from that kit a sheath of the proper length, i.e., one having a total length, from hub to distal end, of ½ or ¾ cm. less than the distance from needle tip to needle clamp can be selected.

Figure 14:
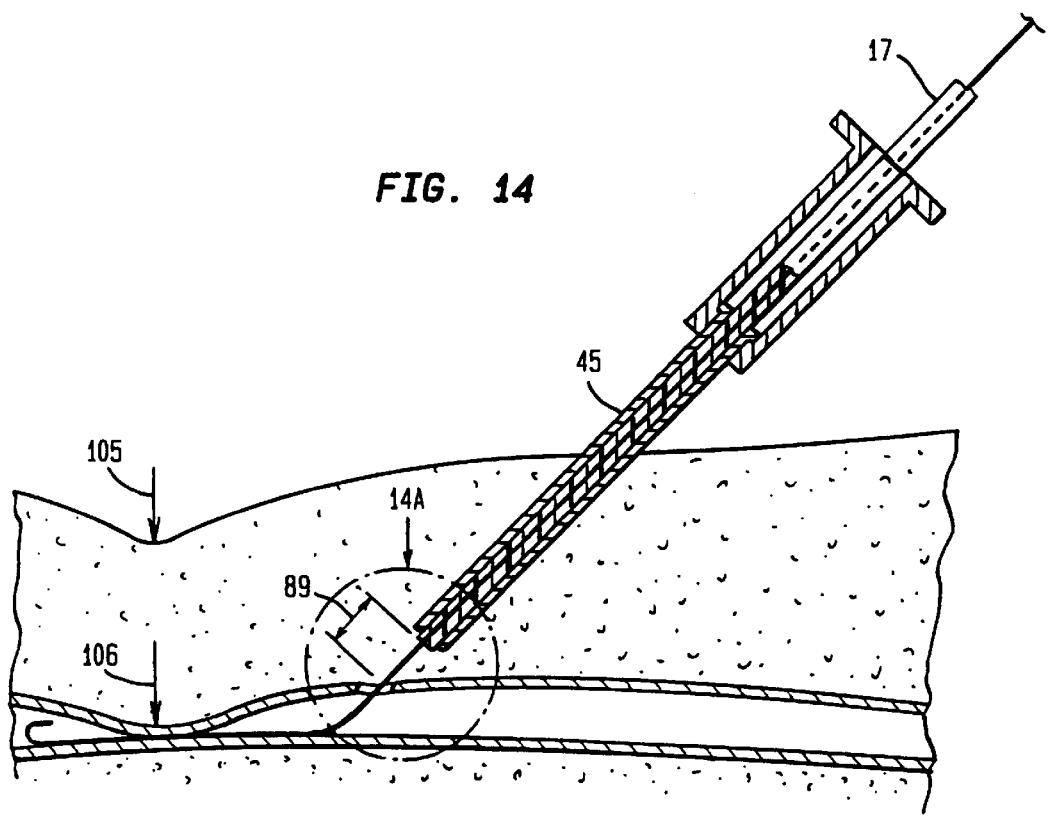

Next, as is best seen in FIG. 14, the sheath 45 is slid down over the dilator, again stopping when its distal tip is about ¾ cm. from the arterial puncture 13. The sheath and dilator can be inserted separately, i.e., in two steps, or together as a unit, in one step.

Figure 14A:
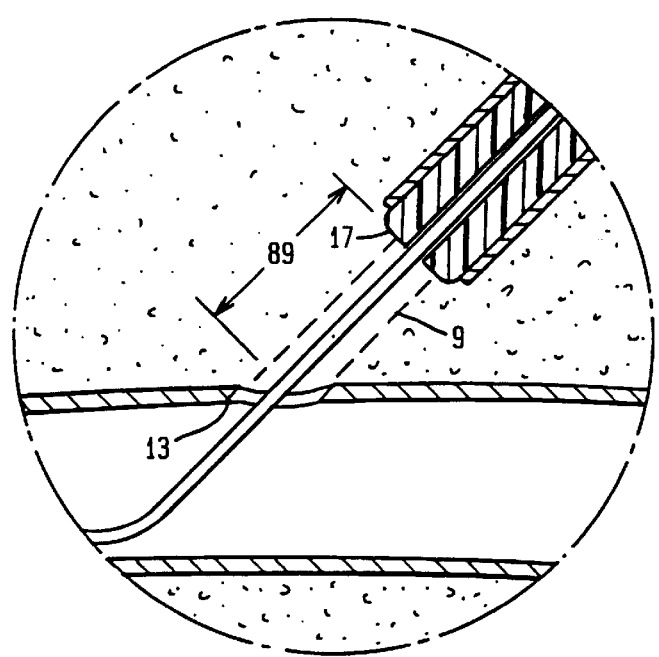
Figure 15:
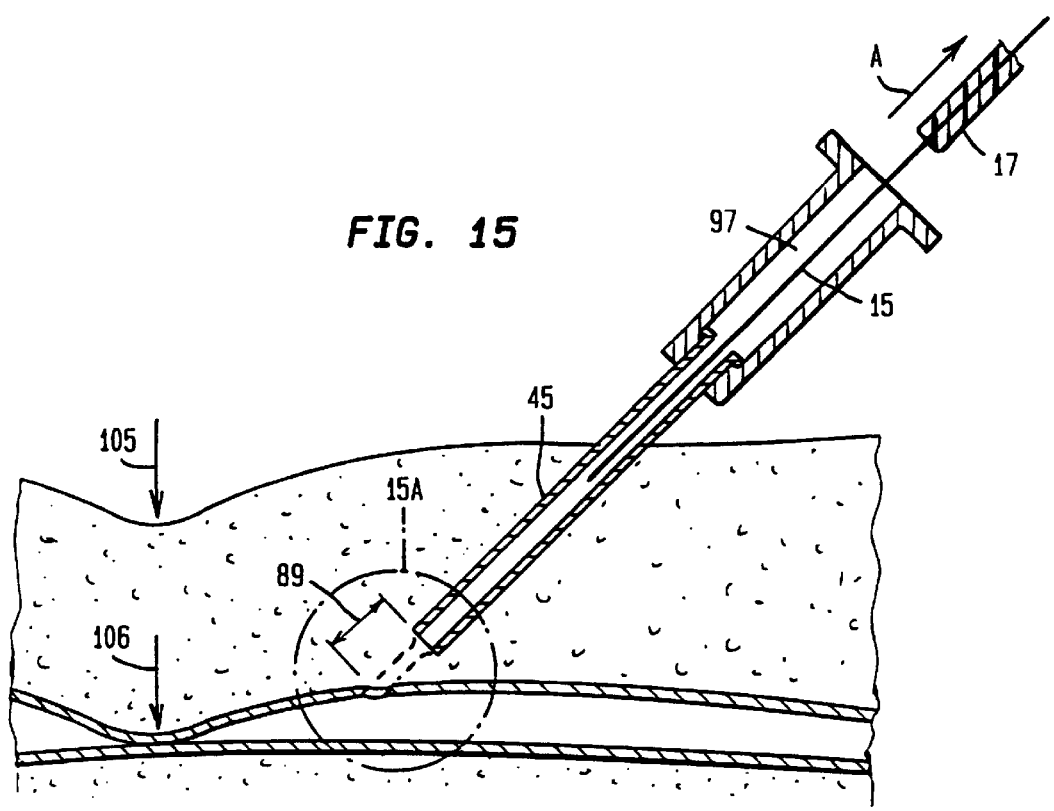
Figure 15A:
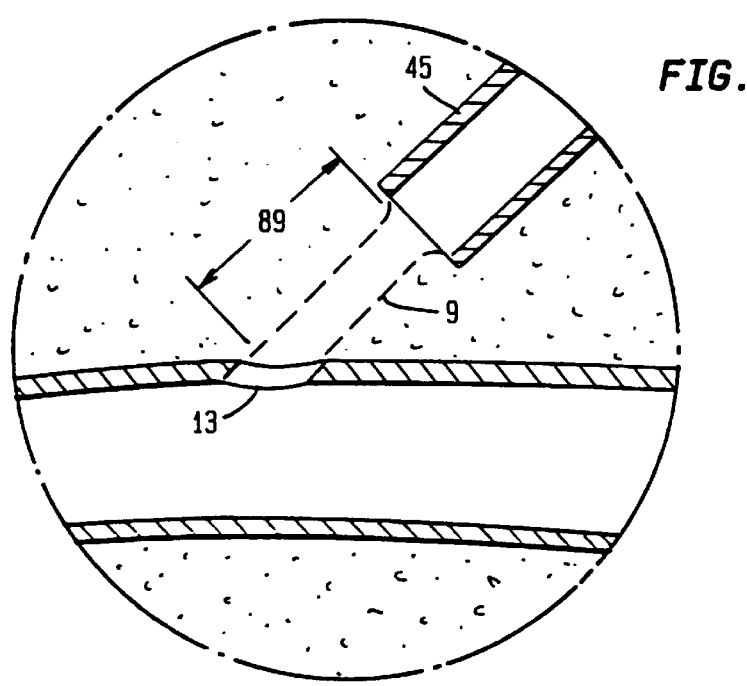

As can be seen in FIGS. 14a and 15a, the partially collapsed section of tissue channel 9 which is immediately adjacent puncture 13 is not reexpanded. Instead, it remains undisturbed.

Figure 17:
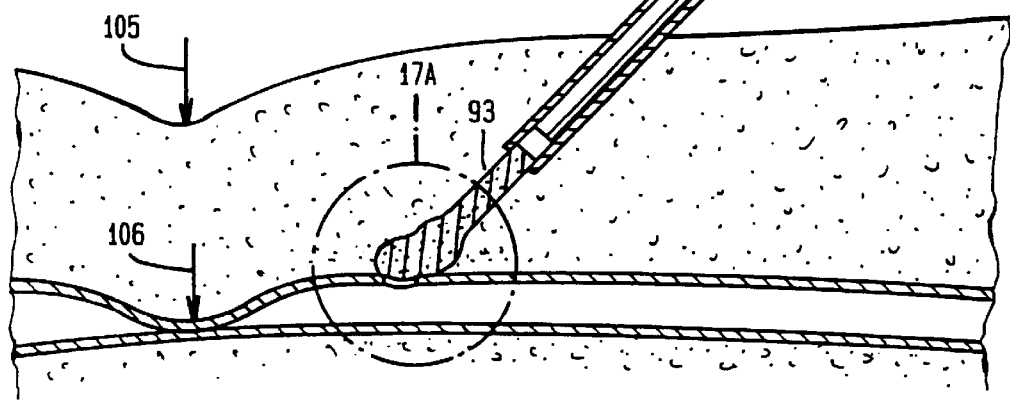
Figure 17A:
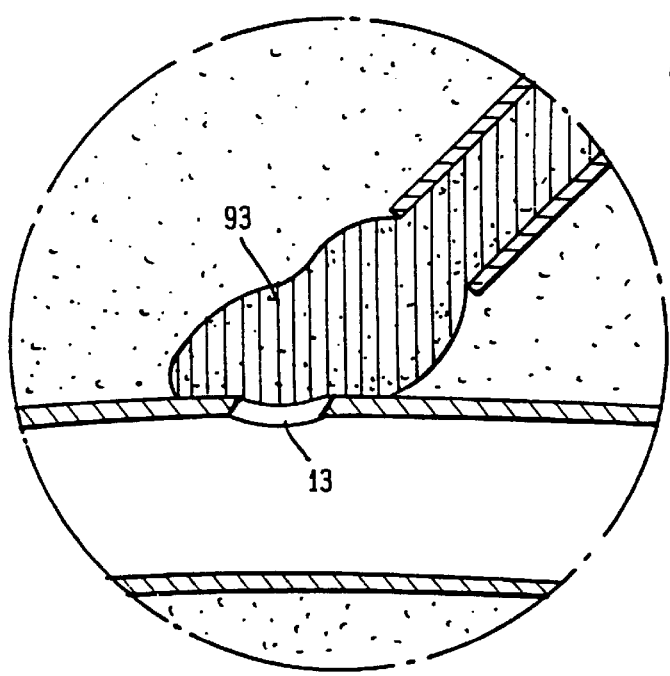

The next step is to withdraw dilator 17 (as is indicated by arrow A on FIG. 15) with guide wire 15 (see FIG. 15), leaving only sheath 45 in tissue channel 9. As depicted in FIG. 16, a preloaded holder or cartridge 91 with plug 93 therein is inserted (see arrow B) into sheath chamber 97. As cartridge 91 is fully seated within chamber 97, a plunger 95 is used to push (see arrow C) plug 93 into and through sheath 45 until the plug exits the sheath so as to cover puncture 13 and fill that section of channel 9 which is adjacent puncture 13 (see FIGS. 17 and 17a). Simultaneously, sheath 45 is slightly withdrawn (indicated by arrows D on FIG. 17) to permit plug 93 to be fully discharged from the sheath.

Plunger 95 is then withdrawn, leaving sheath 45 to maintain pressure on plug 93. Sheath 45 can then be used to hold plug 93 in place over puncture 13 until self sustaining hemostasis has been achieved. Alternatively, as depicted in FIG. 18, a second preloaded holder or cartridge 99 can then be inserted (see arrow E) into chamber 97. Once again, a plunger, 103 is used to push (see arrow F) plug 101 through the sheath. Preferably, plug 101 should be long enough so that when fully discharged from the sheath (as depicted in FIG. 21), it will fill substantially all of channel 9, reaching almost to the surface of the skin.

When the front end of plug 101 reaches the end of sheath 45, it abuts plug 93. Plunger 103 is then used to force about 1 cm. of plug 101 out of the sheath (107 on FIG. 19). In this way, plug 101 takes over the function of holding plug 93 in place against puncture 13. While plunger 103 continues to hold plug 101 in place (see arrow H), sheath 45 is withdrawn from channel 9 (see arrows G on FIG. 20). As can be seen in FIG. 22, when sheath 45 is fully withdrawn, plugs 93 and 101 fill substantially all of channel 9.

It is believed to be most desireable that the front plug 93 be of loosely packed material, while rear plug 101 be of a more densely packed material. Also, as presently contemplated, in its natural, unrestrained state, plug 101 has a cross section larger than that of cartridge 99. Therefore, in order to get it into the cartridge, it must be compressed. It then stays in this compressed state while in cartridge 99 as well as while passing through sheath 45. However, after exiting from sheath 45, it naturally expands and presses against the walls of channel 9. The interaction then between plug 101 and the walls of channel 9 tends to hold the plug in place. As a result, very little if any external pressure is required.

Accordingly, after only a very short period of time, perhaps almost immediately, the plunger can be removed, leaving only the two plugs in the wound (see FIG. 21). Pressure on the artery (see arrows 105 in FIGS. 13–21) can then be released, permitting normal flow through the artery to resume.

Although it is not necessary, in the practice of the method of the instant invention, for plugs 93 and 101 to fill all of channel 9 from artery to skin line, it is believed preferable that they do so. Alternatively, plug 101 can be made longer than necessary to reach the skin line, in which case it could then be cut off flush with the skin. As yet another alternative, a single plug, the size of plugs 93 and 101 combined could be used instead of two separate plugs.

While it is believed most advantageous to remove the procedure cannula and then insert a new sheath, it would be within the scope of the instant invention to use the procedure cannula as the delivery sheath through which the hemostatic material is passed.

It should also be understood that the hemostatic material employed may take many forms. For example, it may be in the form of a liquid or it may have a more viscous paste-like consistency. When using liquid or paste-like materials, the delivery sheath, the hemostatic charge holder and the piston might most advantageously be combined together in a single syringe-like device.

While the method and apparatus of this invention have been described in connection with several specific embodiments, it should be understood that numerous modifications could be made by persons of skill in this art without departing from the scope of this invention. Accordingly, the above description is intended to be merely illustrative and not limiting. The scope of the invention claimed should be understood as including all those alternatives and modifications which the above specification would readily suggest or which would readily occur or be apparent to one skilled in the art upon reading the above.

What is claimed is:

1. A device for inserting hemostatic material through a tissue channel and against the outside wall of a blood vessel of a patient wherein the blood vessel wall has a puncture having a predetermined width therein adjacent the tissue channel, the tissue channel and the puncture having been formed by an original procedure sheath, comprising
   (a) a charge of hemostatic material having a width greater than said predetermined width of the puncture such that said charge of hemostatic material cannot enter the blood vessel through the puncture,
   (b) a hollow insertion sheath adapted to pass through the tissue channel and having an inner diameter, said inner diameter of said insertion sheath being larger than said predetermined width of the puncture whereby said charge of hemostatic material is slidable within said inner diameter of said hollow insertion sheath,
   (c) means for placing said hemostatic material in said hollow insertion sheath, and
   (d) a tissue dilator having a size substantially corresponding to said width of said charge of hemostatic material for slidably engaging said inner diameter of said hollow insertion sheath and for advancing said hemostatic material through said hollow insertion sheath to the outside of the vessel wall around the puncture without ever actually entering the lumen of the blood vessel.

2. The device of claim 1, wherein said charge of hemostatic material is in the form of a liquid.

3. The device of claim 2 wherein said liquid is comprised of fibrin glue.

4. The device of claim 2 wherein said liquid is comprised of thrombin.

5. The device of claim 1, wherein said charge of hemostatic material is in the form of a paste.

6. The device of claim 5 wherein said paste is comprised of fibrin glue.

7. The device of claim 5 wherein said paste is comprised of thrombin.

8. The device of claim 1, wherein said charge of hemostatic material is in the form of a plug of loose fibers.

9. The device of claim 1, wherein said charge of hemostatic material is in the form of a sponge.

10. The device of claim 1, wherein said charge of hemostatic material is in the form of a plug having a front end and a back end and wherein said front end is covered with a membrane of hemostatic material and wherein the remainder of said plug is in the form of a densely packed material.

11. The device of claim 1, wherein said charge of hemostatic material is in the form of a balloon made of collagen membrane.

12. A device for use in sealing a puncture having a predetermined width in a wall of a blood vessel of a patient where the blood vessel is separated from the skin of the patient by a layer of tissue, where a tissue channel communicates between the puncture and the patient's skin and where a guide wire having proximal and distal ends extends at least from the puncture, through the channel, to the patient's skin, the tissue channel and the puncture having been formed by an original procedure sheath, comprising
   (a) a tissue dilator having a front portion and a rear portion, (b) a dilator channel running through said tissue dilator from said front portion to said rear portion, said dilator channel being adapted to receive therein and pass therethrough the proximal end of said guide wire, (c) an elongated hollow insertion sheath having a distal end, a proximal end, and an inner diameter, said inner diameter of said hollow insertion sheath being larger than said predetermined width of the puncture, (d) hemostatic material having a width greater than said predetermined width of the puncture, whereby said hemostatic material is slidable within said inner diameter of said hollow insertion sheath, and said hemostatic material cannot enter the blood vessel through the puncture, and (e) means for inserting said hemostatic material into said hollow insertion sheath, said tissue dilator having a size substantially corresponding to said width of said hemostatic material for slidably engaging said inner diameter of said hollow insertion sheath and for advancing said hemostatic material through said hollow insertion sheath to the outside of the vessel wall around the puncture without ever actually entering the lumen of the blood vessel.

13. The device of claim 12, wherein said hemostatic material is in the form of a plug of loose fibers.

14. The device of claim 12, wherein said hemostatic material is densely packed.

15. The device of claim 12, wherein said hemostatic material is in the form of a plug having a front end and a back end and wherein said front end is covered with a membrane of hemostatic material and wherein the remainder of said plug is in the form of a densely packed sponge of hemostatic material.

16. The device of claim 12, wherein said hemostatic material is in the form of a balloon having a collagen membrane.

* * * * *

UNITED STATES PATENT AND TRADEMARK OFFICE
CERTIFICATE OF CORRECTION

PATENT NO. : 5,830,130
DATED : November 3, 1998
INVENTOR(S) : Janzen et al.

It is certified that error appears in the above-identified patent and that said Letters Patent is hereby corrected as shown below:

Column 1, line 6, "198" should read --183--.

Column 1, line 10, delete "1."

Column 1, line 15, delete "2"

Signed and Sealed this

Twentieth Day of April, 1999

Attest:

Q. TODD DICKINSON

Attesting Officer

Acting Commissioner of Patents and Trademarks